US009303976B2

(12) United States Patent
Uekita et al.

(10) Patent No.: US 9,303,976 B2
(45) Date of Patent: Apr. 5, 2016

(54) SUBSTRATE PROCESSING SYSTEM AND SUBSTRATE PROCESSING PROGRAM

(75) Inventors: Masahiro Uekita, Kanagawa-ken (JP);
Hiroshi Koizumi, Kanagawa-ken (JP);
Tomomichi Naka, Kanagawa-ken (JP);
Naoaki Sakurai, Kanagawa-ken (JP);
Eijiro Koike, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 679 days.

(21) Appl. No.: 13/456,458

(22) Filed: Apr. 26, 2012

(65) Prior Publication Data

US 2012/0277896 A1    Nov. 1, 2012

(30) Foreign Application Priority Data

Apr. 28, 2011    (JP) ................................. 2011-102427

(51) Int. Cl.
| G06F 19/00 | (2011.01) |
| G06F 15/00 | (2006.01) |
| G01B 11/06 | (2006.01) |
| G01N 21/64 | (2006.01) |
| G01N 21/66 | (2006.01) |

(52) U.S. Cl.
CPC ................ *G01B 11/06* (2013.01); *G01N 21/64* (2013.01); *G01N 21/66* (2013.01); *G01N 2021/6421* (2013.01); *H01L 2933/0041* (2013.01)

(58) Field of Classification Search
CPC ....... G01B 11/06; G01N 21/64; G01N 21/66; G01N 2021/6421; H01L 2933/0041
USPC .................................... 700/95, 121; 702/172
See application file for complete search history.

(56) References Cited

U.S. PATENT DOCUMENTS

| 5,361,543 A | * | 11/1994 | Bory ............................. 451/165 |
| 5,910,041 A | * | 6/1999 | Duescher ....................... 451/28 |
| 6,267,648 B1 | * | 7/2001 | Katayama et al. .............. 451/44 |

(Continued)

FOREIGN PATENT DOCUMENTS

| JP | 55-37273 A | 3/1980 |
| JP | 63-102872 A | 5/1988 |

(Continued)

OTHER PUBLICATIONS

Office Action issued Feb. 28, 2013 in Japanese Patent Application No. 2011-102427 (with English-language translation).

(Continued)

*Primary Examiner* — Charles Kasenge
(74) *Attorney, Agent, or Firm* — Oblon, McClelland, Maier & Neustadt, L.L.P.

(57) ABSTRACT

According to one embodiment, a substrate processing system includes a measuring unit, a data processing unit, and a processing unit. The measuring unit is configured to measure information relating to a thickness dimension of a substrate. The substrate includes a light emitting unit and a wavelength conversion unit. The wavelength conversion unit includes a phosphor. The data processing unit is configured to determine processing information relating to a thickness direction of the wavelength conversion unit based on the measured information relating to the thickness dimension of the substrate and based on information relating to a characteristic of light emitted from the light emitting unit. The processing unit is configured to perform processing of the wavelength conversion unit based on the determined processing information.

25 Claims, 5 Drawing Sheets

(56) References Cited

U.S. PATENT DOCUMENTS

| | | | |
|---|---|---|---|
| 6,329,111 B1* | 12/2001 | Nojiri et al. | 430/25 |
| 6,336,845 B1* | 1/2002 | Engdahl et al. | 451/41 |
| 6,337,536 B1* | 1/2002 | Matsubara et al. | 313/498 |
| 6,528,796 B1* | 3/2003 | Kaifu et al. | 250/370.11 |
| 6,641,341 B2* | 11/2003 | Sato et al. | 409/137 |
| 6,753,972 B1* | 6/2004 | Hirose et al. | 356/630 |
| 6,806,970 B2* | 10/2004 | Hirose et al. | 356/630 |
| 6,853,010 B2* | 2/2005 | Slater et al. | 257/98 |
| 6,893,781 B2* | 5/2005 | Nonaka et al. | 430/7 |
| 7,023,019 B2* | 4/2006 | Maeda et al. | 257/89 |
| 7,256,057 B2* | 8/2007 | Schardt et al. | 438/14 |
| 7,329,991 B2* | 2/2008 | Miyashita et al. | 313/587 |
| 7,501,657 B2* | 3/2009 | Nagai | 257/79 |
| 7,528,077 B2* | 5/2009 | Izuno et al. | 438/778 |
| 7,585,205 B2* | 9/2009 | Katsuoka et al. | 451/9 |
| 7,727,873 B2* | 6/2010 | Sato et al. | 438/604 |
| 7,855,501 B2* | 12/2010 | Tanimoto et al. | 313/503 |
| 8,079,788 B2* | 12/2011 | Murota et al. | 409/134 |
| 8,093,079 B2* | 1/2012 | Kim | 438/29 |
| 8,164,254 B2* | 4/2012 | Maruyama et al. | 313/506 |
| 8,217,568 B2* | 7/2012 | Matsumura | 313/501 |
| 8,253,326 B2* | 8/2012 | Maruyama et al. | 313/506 |
| 8,324,001 B2* | 12/2012 | Kim | 438/29 |
| 8,361,819 B2* | 1/2013 | Kim | 438/29 |
| 8,399,275 B2* | 3/2013 | Akimoto et al. | 438/46 |
| 8,877,524 B2* | 11/2014 | Chitnis et al. | 438/14 |
| 2002/0112331 A1* | 8/2002 | Yamada | 29/33.5 |
| 2005/0151147 A1* | 7/2005 | Izuno et al. | 257/98 |
| 2006/0273324 A1* | 12/2006 | Asai et al. | 257/79 |
| 2007/0046169 A1* | 3/2007 | Maeda et al. | 313/487 |
| 2007/0268032 A1* | 11/2007 | Yoshioka et al. | 324/754 |
| 2007/0275544 A1* | 11/2007 | Maki et al. | 438/464 |
| 2008/0135862 A1* | 6/2008 | Maeda et al. | 257/98 |
| 2008/0137106 A1* | 6/2008 | Ono | 356/630 |
| 2008/0247835 A1* | 10/2008 | Murota et al. | 409/134 |
| 2009/0001869 A1* | 1/2009 | Tanimoto et al. | 313/502 |
| 2009/0239388 A1* | 9/2009 | Izuno et al. | 438/778 |
| 2009/0261358 A1* | 10/2009 | Chitnis et al. | 257/88 |
| 2010/0248400 A1* | 9/2010 | Kim | 438/15 |
| 2010/0289405 A1* | 11/2010 | Maruyama et al. | 313/503 |
| 2010/0308357 A1* | 12/2010 | Horie et al. | 257/98 |
| 2011/0294240 A1* | 12/2011 | Kim | 438/16 |
| 2011/0297987 A1 | 12/2011 | Koizumi et al. | |

FOREIGN PATENT DOCUMENTS

| | | | |
|---|---|---|---|
| JP | 2002-158377 A | 5/2002 | |
| JP | 2003-46134 A | 2/2003 | |
| JP | 2005-224900 A | 8/2005 | |
| JP | 2007-66969 A | 3/2007 | |
| JP | 2008-150225 A | 7/2008 | |
| JP | 2008-541411 A | 11/2008 | |
| JP | 2009-158541 A | 7/2009 | |
| JP | 2010-17787 A | 1/2010 | |
| JP | 2010-27704 A | 2/2010 | |
| JP | 2010-157637 | 7/2010 | |
| JP | 2010-177620 A | 8/2010 | |
| JP | 2010-541284 A | 12/2010 | |
| JP | 2011-517090 | 5/2011 | |
| WO | WO 2006/121197 A1 | 11/2006 | |
| WO | WO 2009/045924 A1 | 4/2009 | |
| WO | WO 2009/123726 A2 | 10/2009 | |

OTHER PUBLICATIONS

U.S. Appl. No. 13/419,684, filed Mar. 14, 2012, Hiroshi Koizumi, et al.
Office Action issued Sep. 27, 2013, in Japanese Patent Application No. 2011-102427 (with English-language translation).
Office Action issued Dec. 22, 2014 in Japanese Patent Application No. 2011-102427 (with English language translation).
Japanese Office Action issued Dec. 11, 2014 in Patent Application No. 2014-055272 (with English Translation).
Japanese Office Action dated Jun. 9, 2015, issued in Japanese Patent Application No. 2014-055272 (with English translation).
Office Action issued on Oct. 7, 2015 in Japanese Patent Application No. 2014-055272 with English translation.

* cited by examiner

SUBSTRATE PROCESSING SYSTEM AND SUBSTRATE PROCESSING PROGRAM

CROSS-REFERENCE TO RELATED APPLICATIONS

This application is based upon and claims the benefit of priority from the prior Japanese Patent Application No. 2011-102427, filed on Apr. 28, 2011; the entire contents of which are incorporated herein by reference.

FIELD

Embodiments described herein relate generally to a substrate processing system and substrate processing program.

BACKGROUND

There exists a semiconductor light emitting device that uses a semiconductor light emitting element (hereinbelow, called simply the light emitting element) and a wavelength conversion unit including a phosphor to obtain white light by, for example, using a light emitting element that emits blue light (e.g., a blue LED (Light Emitting Diode)) and a phosphor that emits yellow light which has a complementary color relationship with blue.

When manufacturing such a semiconductor light emitting device, there exists technology to polish the surface of the wavelength conversion unit to become flat and smooth, and subsequently perform wet etching to create a microstructure on the surface.

However, even in the case where the surface is polished to be smooth and the microstructure is made in the smooth surface, chromaticity unevenness undesirably increases with the wavelength unevenness of the light emitted from the light emitting element because it is difficult to provide a distribution to the amount of the phosphor included in the wavelength conversion unit.

DETAILED DESCRIPTION

Figure 1:
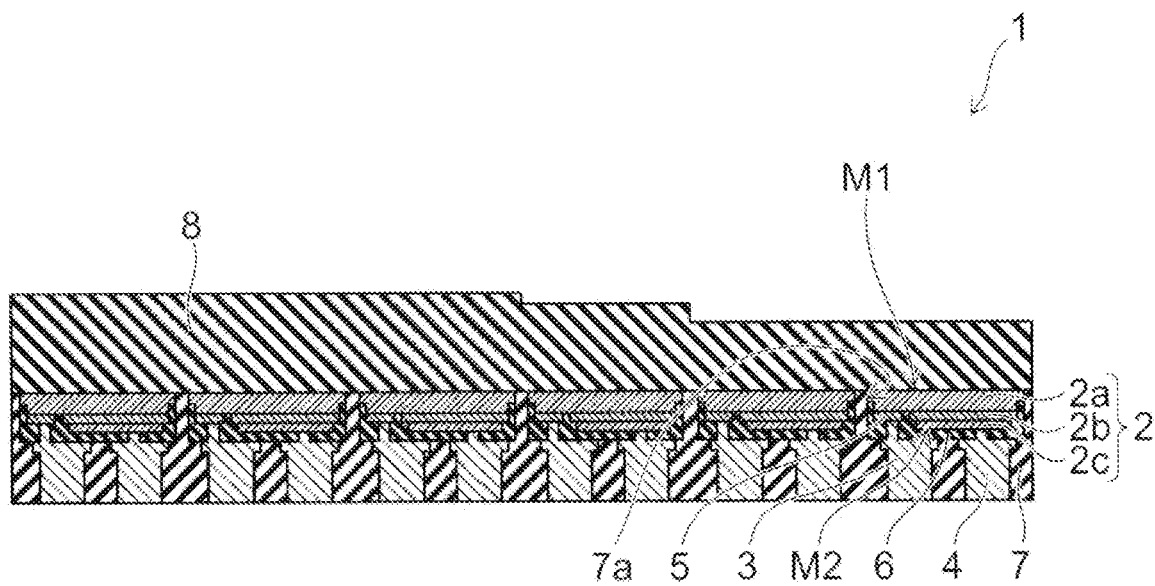
FIG. 1 is a schematic cross-sectional view illustrating an example of a semiconductor light emitting device for which processing has been performed.

In general, according to one embodiment, a substrate processing system includes a measuring unit, a data processing unit, and a processing unit. The measuring unit is configured to measure information relating to a thickness dimension of a substrate. The substrate includes a light emitting unit and a wavelength conversion unit. The wavelength conversion unit includes a phosphor. The data processing unit is configured to determine processing information relating to a thickness direction of the wavelength conversion unit based on the measured information relating to the thickness dimension of the substrate and based on information relating to a characteristic of light emitted from the light emitting unit. The processing unit is configured to perform processing of the wavelength conversion unit based on the determined processing information.

Embodiments will now be illustrated with reference to the drawings. Similar components in the drawings are marked with like reference numerals; and a detailed description is omitted as appropriate.

First, a semiconductor light emitting device which can be a processing object will be illustrated.

Herein, as an example, a semiconductor light emitting device including multiple light emitting units (a so-called multi-chip semiconductor light emitting device) will be illustrated.

FIG. 1 is a schematic cross-sectional view illustrating an example of a semiconductor light emitting device for which processing has been performed.

As illustrated in FIG. 1, the semiconductor light emitting device 1 includes a light emitting unit 2, an electrode unit 3, an electrode unit 4, a bonding unit 5, an insulating unit 6, a sealing unit 7, and a wavelength conversion unit 8.

The light emitting unit 2 has a major surface M1 and a major surface M2 which is the surface opposite to the major surface M1; and the light emitting unit 2 is multiply provided.

A semiconductor portion 2a, an active portion 2b, and a semiconductor portion 2c are provided in the light emitting unit 2 which is configured to emit light.

The semiconductor portion 2a may be formed using an n-type nitride semiconductor such as, for example, GaN (gallium nitride), AlN (aluminum nitride), AlGaN (aluminum gallium nitride), InGaN (indium gallium nitride), etc.

The active portion 2b is provided between the semiconductor portion 2a and the semiconductor portion 2c.

The active portion 2b may have a quantum well structure including a well layer configured to produce light by the recombination of holes and electrons and a barrier layer (a clad layer) having a bandgap larger than that of the well layer.

However, the configuration of the active portion 2b is not limited to a quantum well structure; and a structure that is capable of emitting light may be appropriately selected.

The semiconductor portion 2c may be formed using a p-type nitride semiconductor such as, for example, GaN, AlN, AlGaN, InGaN, etc.

The light emitting unit 2 may be, for example, a light emitting diode having a peak light emission wavelength of 350 nm to 600 nm.

The electrode unit 3 and the electrode unit 4 are provided to pierce between the bottom surface of a recess 7a and the end surface of the sealing unit 7.

One end portion of the electrode unit 3 is electrically connected to the bonding unit 5; and the electrode unit 3 is electrically connected to the semiconductor portion 2a via the bonding unit 5.

One end portion of the electrode unit 4 is electrically connected to the semiconductor portion 2c.

The bonding unit 5 is provided between the electrode unit 3 and the semiconductor portion 2a. The bonding unit 5 may be formed using, for example, a metal material such as Cu (copper), etc. The bonding unit 5 is not always necessary and may be appropriately provided if necessary.

The insulating unit 6 is provided to fill the recess 7a which is provided in the sealing unit 7. The insulating unit 6 may be formed from, for example, a resin, an inorganic material such as $SiO_2$, and the like.

The sealing unit 7 is provided on the major surface M2 side of the light emitting unit 2 to seal the electrode unit 3 and the electrode unit 4 while leaving the end portion of the electrode unit 3 and the end portion of the electrode unit 4 exposed.

The sealing unit 7 has the recess 7a and performs the role of sealing the light emitting unit 2 and the bonding unit 5 provided in the interior of the recess 7a. The sealing unit 7 and the insulating unit 6 may be formed integrally.

The wavelength conversion unit 8 is provided on the major surface M1 side of the light emitting unit 2 and contains a phosphor that is described below. The wavelength conversion unit 8 has a distribution of the amount of the phosphor based on information relating to a characteristic of the light emitted from the light emitting unit 2. Details relating to the distribution of the amount of the phosphor are described below.

The wavelength conversion unit 8 may be formed using a resin in which a phosphor capable of wavelength conversion is mixed and the like.

The wavelength conversion unit 8 may include at least one type of the phosphors having the peak light emission wavelengths of not less than 440 nm and not more than 470 nm (blue), not less than 500 nm and not more than 555 nm (green), not less than 560 nm and not more than 580 nm (yellow), and not less than 600 nm and not more than 670 nm (red). The wavelength conversion unit 8 may include a phosphor having a band of the light emission wavelength of 380 nm to 720 nm.

The phosphor may include at least one type of element selected from the group consisting of silicon (Si), aluminum (Al), titanium (Ti), germanium (Ge), phosphorus (P), boron (B), yttrium (Y), alkaline earth element, sulfide element, rare-earth element, and nitride element.

Materials of the phosphor configured to emit a red fluorescence are, for example, as follows. However, the phosphor configured to emit the red fluorescence is not limited to the following and may be modified appropriately.

$La_2O_2S$:Eu, Sm
$LaSi_3N_5$: $Eu^{2+}$
α-sialon:$Eu^{2+}$
$CaAlSiN_3$: $Eu^{2+}$
$(SrCa)AlSiN_3$: $Eu^{X+}$
$Sr_x(Si_yAl_3)_z(O_xN)$:$Eu^{X+}$ Materials of the phosphor configured to emit a green fluorescence are, for example, as follows. However, the phosphor configured to emit the green fluorescence is not limited to the following and may be modified appropriately.

(Ba, Sr, Mg)O.a$Al_2O_3$:Mn
$(BrSr)SiO_4$:Eu
α-sialon:$Yb^{2+}$
β-sialon: $Eu^{2+}$
$(CaSr)Si_2O_4N_7$: $Eu^{2+}$
Sr(SiAl)(ON):Ce Materials of the phosphor configured to emit a blue fluorescence are, for example, as follows. However, the phosphor configured to emit the blue fluorescence is not limited to the following and may be modified appropriately:

ZnS:Ag, Cu, Ga, Cl
(Ba, Eu)$MgAl_{10}O_{17}$
(Ba, Sr, Eu)(Mg, Mn)$Al_{10}O_{17}$
10(Sr, Ca, Ba, Eu).$6PO_4.Cl_2$
$BaMg_2Al_{16}O_{25}$:Eu
$Y_3(Al, Ga)_5O_{12}$:Ce
$SrSi_2ON_{2.7}$:$Eu^{2+}$

Materials of the phosphor configured to emit a yellow fluorescence are, for example, as follows. However, the phosphor configured to emit the yellow fluorescence is not limited to the following and may be modified appropriately.

Li(Eu, Sm)$W_2O_8$
$(Y, Gd)_3, (Al, Ga)_5O_{12}$:$Ce^{3+}$
$Li_2SrSiO_4$:$Eu^{2+}$
$(Sr(Ca, Ba))_3SiO_5$:$Eu^{2+}$
$SrSi_2ON_{2.7}$:$Eu^{2+}$

Materials of the phosphor configured to emit a yellowish green fluorescence are, for example, as follows. However, the phosphor configured to emit the yellowish green fluorescence is not limited to the following and may be modified appropriately.

$SrSi_2ON_{2.7}$:$Eu^{2+}$

It is unnecessary for the mixed phosphor to be of one type; and multiple types of phosphors may be mixed. In such a case, the mixture proportion of the multiple types of phosphors may be changed to change the tint of the light to be white light with a blue tint, white light with a yellow tint, etc.

The resin into which the phosphor is mixed may include, for example, an epoxy resin, a silicone-based resin, a methacrylic resin (PMMA), polycarbonate (PC), cyclic polyolefin (COP), alicyclic acrylic (OZ), allyl diglycol carbonate (ADC), an acrylic resin, a fluorocarbon resin, a hybrid resin of a silicone-based resin and an epoxy resin, a urethane resin, etc.

Here, although the light emitting unit 2 may be formed by, for example, epitaxial growth and the like, there are cases where fluctuation occurs in the thickness dimension of the light emitting unit 2 in the formation processes. Then, the wavelength of the light, i.e., the characteristic of the light, that is emitted from the light emitting unit 2 fluctuates in the case where the fluctuation of the thickness dimension of the light emitting unit 2 occurs.

Then, in the case where the wavelength of the light emitted from the light emitting unit 2 fluctuates, the chromaticity also fluctuates.

Figure 2:
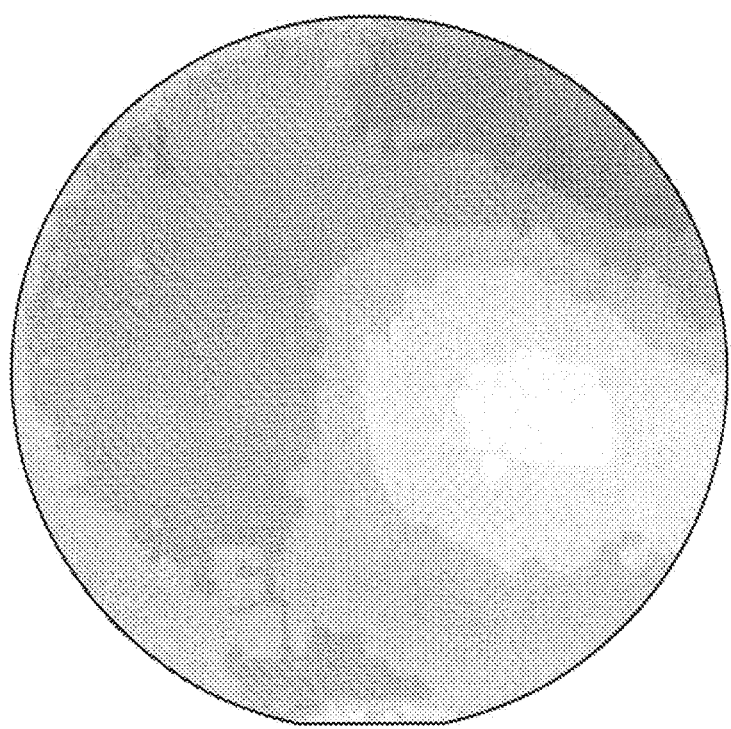
FIG. 2 is a schematic view illustrating the distribution of the wavelength of the light emitted from the multiple light emitting units formed on the substrate.

FIG. 2 is a schematic view illustrating the distribution of the wavelength of the light emitted from the multiple light emitting units formed on the substrate.

The distribution of the wavelength of the light emitted from the multiple light emitting units formed on the substrate is illustrated by monotone shading such that shorter wavelengths of the light are dark and longer wavelengths of the light are light.

As illustrated in FIG. 2, there are cases where the wavelength of the light emitted from the light emitting unit differs by position on the substrate.

This means that there is fluctuation in the wavelength of the light emitted from the light emitting unit 2 that is formed.

Here, there is a risk that the chromaticity unevenness may increase if there is fluctuation in the wavelength of the light.

Therefore, the wavelength conversion unit 8 having a thickness dimension changed based on the wavelength unevenness of the light emitted from the light emitting unit 2 is provided. In other words, the wavelength conversion unit 8 having a distribution of the amount of the phosphor based on the information relating to the characteristic of the light emitted from the light emitting unit 2 is provided.

The relationship between the thickness dimension of the wavelength conversion unit 8 and the chromaticity unevenness will now be illustrated.

Figure 3A:
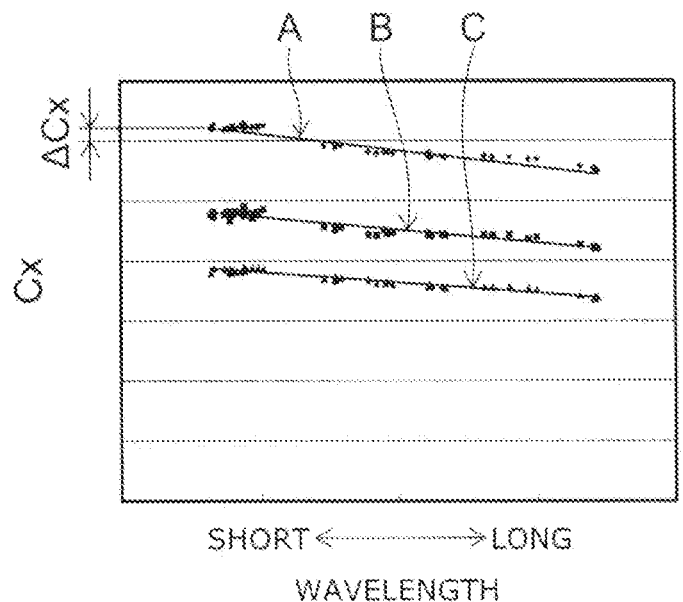
FIGS. 3A and 3B are schematic graphs illustrating the relationship between the wavelength and the chromaticity.
Figure 3B:
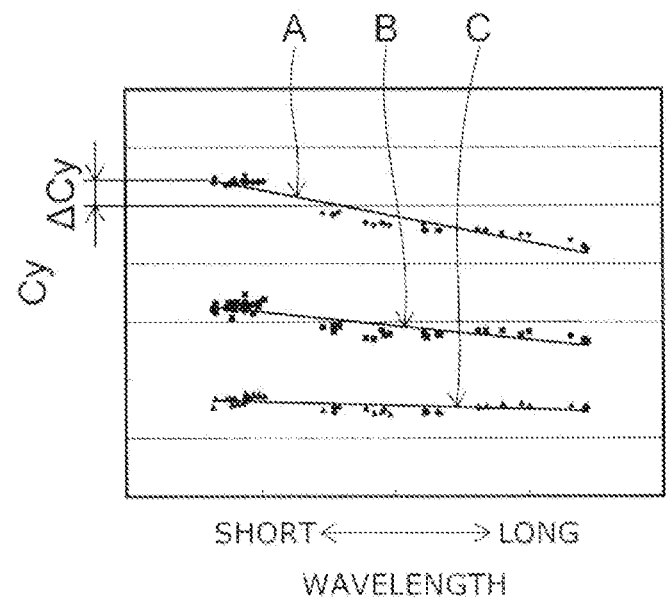

FIGS. 3A and 3B are schematic graphs illustrating the relationship between the wavelength and the chromaticity.

FIG. 3A is a schematic graph illustrating the relationship between the wavelength and a value Cx of the X coordinate of the chromaticity diagram; and FIG. 3B is a schematic graph illustrating the relationship between the wavelength and a value Cy of the Y coordinate of the chromaticity diagram.

In FIGS. 3A and 3B, A is the case where the thickness dimension of the wavelength conversion unit is about 100 μm, B is the case where the thickness dimension of the wavelength conversion unit is about 65 μm, and C is the case where the thickness dimension of the wavelength conversion unit is about 45 μm. These are cases where the proportion of the amount of the phosphor included in the wavelength conversion unit is constant.

As illustrated in FIGS. 3A and 3B, both the value Cx of the X coordinate and the value Cy of the Y coordinate of the chromaticity diagram decrease as the wavelength lengthens.

This means that the chromaticity also fluctuates in the case where the wavelength of the light emitted from the light emitting unit 2 fluctuates.

Also, both the value Cx of the X coordinate and the value Cy of the Y coordinate of the chromaticity diagram decrease as the thickness dimension of the wavelength conversion unit 8 becomes thin.

This means that the value Cx of the X coordinate and the value Cy of the Y coordinate of the chromaticity diagram can be reduced if the amount of the phosphor included in the wavelength conversion unit 8 is reduced.

In other words, it can be seen that the chromaticity unevenness can be suppressed by controlling the amount of the phosphor included in the wavelength conversion unit 8 based on the wavelength of the light emitted from the light emitting unit 2.

For example, for A, B, and C of FIGS. 3A and 3B, the difference of the value Cx and the value Cy between the light emitting units 2 that emit light of short wavelengths (the left side in the drawings) and the light emitting units 2 that emit light of long wavelengths (the right side in the drawings) can be reduced by reducing the value Cx and the value Cy of the light emitting units 2 that emit the light of the short wavelengths by reducing the amount of the phosphor included in the wavelength conversion unit 8 formed on the light emitting units 2 that emit the light of the short wavelengths.

Therefore, the chromaticity unevenness can be reduced by providing a distribution of the amount of the phosphor of the wavelength conversion unit 8 such that the amount of the phosphor at the positions where the wavelength of the light is short is less than the amount of the phosphor at the positions where the wavelength of the light is long.

For example, as in the wavelength conversion unit 8 illustrated in FIG. 1, the chromaticity unevenness can be reduced by providing a distribution of the amount of the phosphor by changing the thickness dimension based on the wavelength of the light emitted from the light emitting unit 2.

In such a case, the amount of the phosphor may be determined such that a chromaticity difference ΔCx, which is the difference between the value Cx of the short wavelength side and the value Cx of the long wavelength side, is not more than 0.015.

The amount of the phosphor may be determined such that a chromaticity difference ΔCy, which is the difference between the value Cy of the short wavelength side and the value Cy of the long wavelength side, is not more than 0.015.

Because the chromaticity difference ΔCx and the chromaticity difference ΔCy change together when changing the amount of the phosphor, the amount of the phosphor may be determined such that the greater of the chromaticity difference ΔCx and the chromaticity difference ΔCy is not more than 0.015.

In such a case, it is sufficient for the chromaticity difference ΔCx and the chromaticity difference ΔCy to be not more than 0.015 at least between adjacent light emitting units 2.

In the case where the light emitting unit 2 is multiply provided, it is sufficient to subdivide the light emitting unit 2 and determine the amount of the phosphor for each of the subdivided regions such that the chromaticity difference ΔCx and the chromaticity difference ΔCy are not more than 0.015.

Thus, the wavelength conversion unit 8 has a distribution of the amount of the phosphor corresponding to the change of the thickness dimension. Such a wavelength conversion unit 8 may be formed by cutting away the front surface side of the wavelength conversion unit 8 based on the characteristic of the light emitted from the light emitting unit 2 (e.g., the wavelength of the light emitted from the light emitting unit 2).

In such a case, to perform the chromaticity correction by cutting away the front surface side of the wavelength conversion unit 8, it is necessary to perform processing with micron-order precision for the front surface side of the wavelength conversion unit that was formed with a uniform thickness.

A substrate processing system 100 that can perform processing to suppress the chromaticity unevenness of the semiconductor light emitting device 1, i.e., the substrate processing system 100 that can perform processing of the front surface side of the wavelength conversion unit 8 with micron-order precision, will now be illustrated.

First Embodiment

Figure 4:
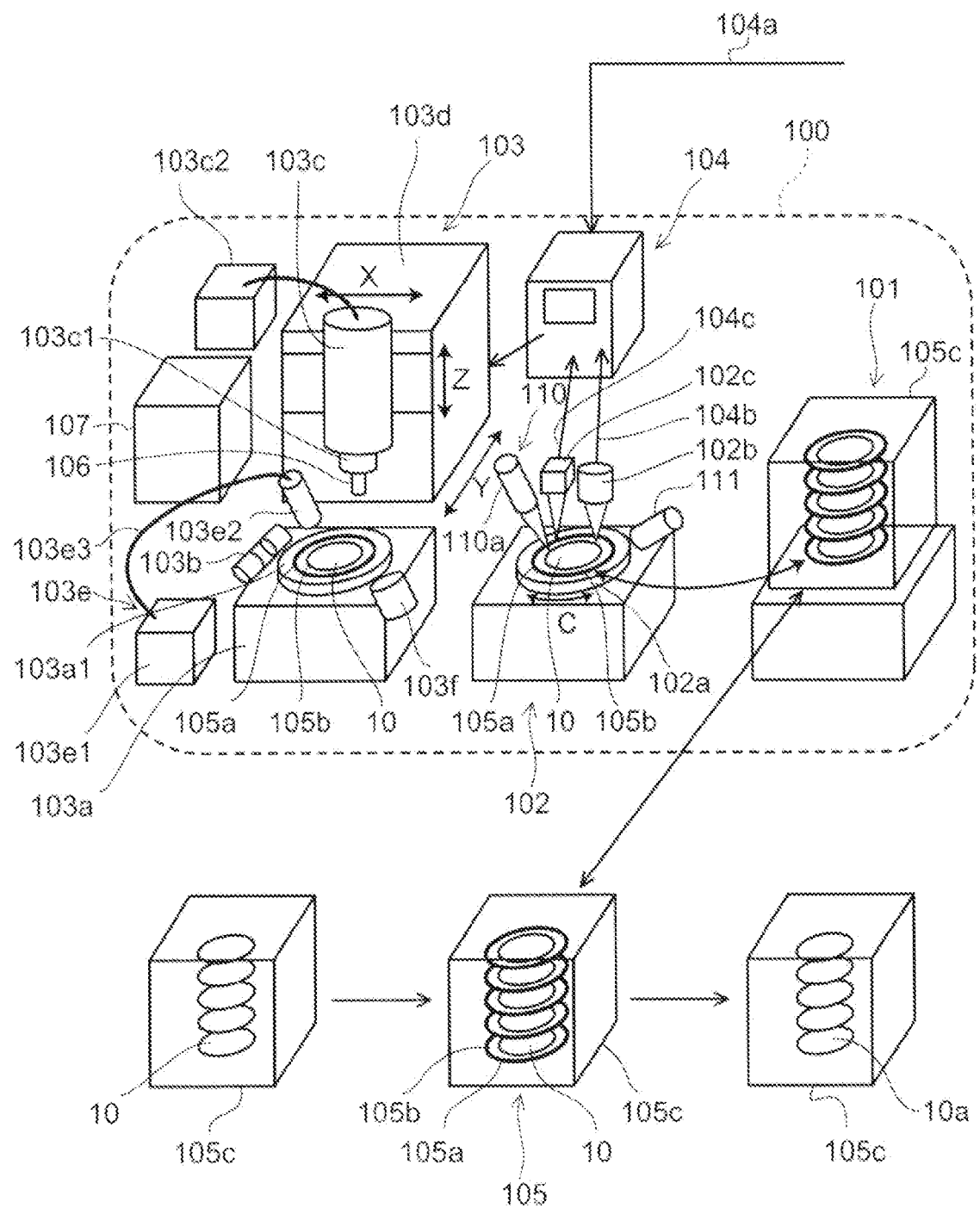
FIG. 4 is a schematic view illustrating a substrate processing system according to a first embodiment.

FIG. 4 is a schematic view illustrating a substrate processing system according to a first embodiment.

Figure 5:
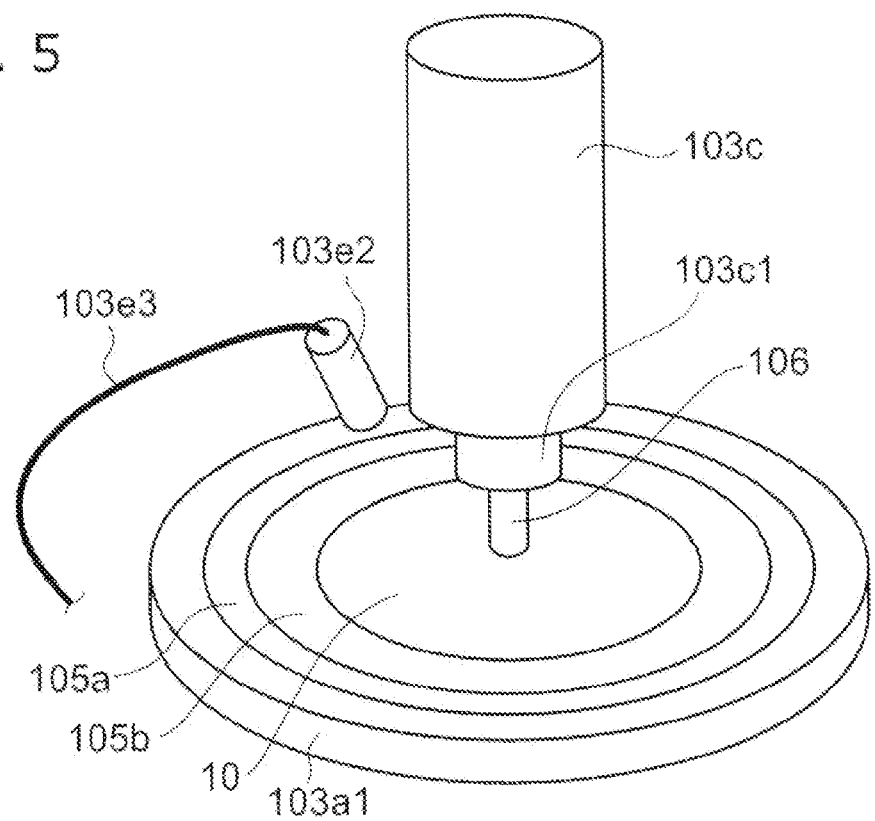
FIG. 5 is a schematic view illustrating the main components of the processing unit.

FIG. 5 is a schematic view illustrating the main components of the processing unit.

As illustrated in FIG. 4 and FIG. 5, the substrate processing system 100 includes a placement unit 101, a detection unit 102, a processing unit 103, and a data processing unit 104.

An attaching/removing unit 105 may be provided to cause a substrate 10 to be held by a holder 105a and to remove a processed substrate 10a from the holder 105a.

In the specification, the substrate 10 is taken to include a wavelength conversion unit formed with a uniform thickness. For example, the substrate 10 may be the semiconductor light emitting device including the wavelength conversion unit before the processing of the front surface side is performed.

The substrate 10a is taken to include the wavelength conversion unit for which the processing of the front surface side has been performed. For example, the substrate 10a may be the semiconductor light emitting device 1 including the wavelength conversion unit for which the front surface side has been cut away.

The attaching/removing unit 105 will now be illustrated.

The holder 105a may be, for example, a plate-like body formed using a metal and the like. A holding unit 105b is provided for holding the substrate 10 at one major surface of the holder 105a. The holding unit 105b may be, for example, a tape and the like that is adhesive. For example, the holding unit 105b may be a dicing tape, etc. The major surface of the holder 105a on the side opposite to the major surface on the side where the holding unit 105b is provided is used as a placement surface when placing the holder 105a at the detection unit 102 and the processing unit 103.

Because deformation of the substrate 10 can be suppressed by the substrate 10 being held by the holder 105a, the precision of the measuring and the processing described below can be increased. Protection and the like can be realized when transferring the substrate 10 by the substrate 10 being held by the holder 105a.

A not-illustrated attaching/removing mechanism for causing the substrate 10 to be held by the holding unit 105b is provided in the attaching/removing unit 105. For example, an attaching apparatus that adheres the substrate 10 to the holder 105a, i.e., the dicing tape, and the like are examples of the not-illustrated attaching/removing mechanism.

A carrier 105c may be placed in the attaching/removing unit 105 to contain the substrate 10, the processed substrate 10a (e.g., the semiconductor light emitting device 1 illustrated in FIG. 1), and the holder 105a that holds the substrate 10 and the substrate 10a.

The carrier 105c may be, for example, a wafer carrier or the like that is capable of containing the substrate 10, the substrate 10a, the holder 105a that holds the substrate 10, and the holder 105a that holds the processed substrate 10a in a stacked configuration (a multiple level configuration). For example, a FOUP (Front Opening Unified Pod), which is a front-opening carrier used to transfer and store the substrates in mini-environment type semiconductor plants, and the like may be used.

Effects of the attaching/removing unit 105 will now be illustrated.

First, the carrier 105c in which the substrate 10 is contained is transferred to the attaching/removing unit 105 and placed in the attaching/removing unit 105. In the attaching/removing unit 105, the substrate 10 is extracted from the carrier 105c; and the not-illustrated attaching/removing mechanism causes the holder 105a to hold the substrate 10.

The holder 105a that holds the substrate 10 is contained in the carrier 105c. The carrier 105c in which the holder 105a that holds the substrate 10 is contained is transferred to the placement unit 101 and placed in the placement unit 101. Subsequently, the holder 105a that holds the substrate 10 is extracted from the carrier 105c; and the prescribed processing of the wavelength conversion unit is performed. The processing of the wavelength conversion unit is described below.

Then, the holder 105a that holds the processed substrate 10a is contained in the carrier 105c. Then, the carrier 105c in which the holder 105a that holds the substrate 10a is contained is transferred to the attaching/removing unit 105 from the placement unit 101 and placed in the attaching/removing unit 105. In the attaching/removing unit 105, the holder 105a that holds the substrate 10a is extracted from the carrier 105c; and the substrate 10a is removed from the holder 105a by the not-illustrated attaching/removing mechanism. The removed substrate 10a is contained in the carrier 105c. The carrier 105c in which the substrate 10a is contained is transferred to the back-end processes (e.g., the dicing process, etc.).

The placement unit 101, the detection unit 102, the processing unit 103, and the data processing unit 104 will now be illustrated.

The placement unit 101 places and holds the carrier 105c.

A holding unit 102a, a position recognition unit 102b, and a measuring unit 102c are provided in the detection unit 102.

The holding unit 102a is for placing and holding the holder 105a that holds the substrate 10 or the substrate 10a. For example, a porous vacuum chuck, a fine groove vacuum chuck, an electrostatic chuck, a freezing chuck, and the like are examples of the holding unit 102a.

The position recognition unit 102b detects the positional information of the substrate 10 by recognizing an alignment mark provided in the substrate 10. For example, an image recognition apparatus including an objective lens, a light source, a CCD camera, and the like is an example of the position recognition unit 102b. However, the position recognition unit 102b is not limited to the image recognition apparatus and may be modified appropriately according to the size of the substrate 10, the detection precision, and the like.

Positional information 104b detected by the position recognition unit 102b is used as the reference for the detection position during the measurement by the measuring unit 102c.

After the alignment mark is recognized, the alignment mark may be brought to a prescribed position by a not-illustrated moving unit that changes the position of the substrate 10. For example, the alignment mark may be brought to the prescribed position by changing the position of the substrate 10 in a rotational axis direction C.

The measuring unit 102c measures information 104c relating to the thickness dimension of the substrate 10 including the wavelength conversion unit that includes the phosphor. For example, the dimension from the front surface of the holding unit 102a (the placement surface of the holder 105a) to the front surface of the wavelength conversion unit may be measured before processing is performed for the front surface side. For example, a displacement sensor such as a non-contact laser displacement sensor and the like are examples of the measuring unit 102c. However, this sensor is not limited to the displacement sensor and may be modified appropriately according to the measurement time, the number of the measurement points, the measurement resolution, and the like.

The information 104c relating to the thickness dimension of the substrate 10 that is measured by the measuring unit 102c is transmitted to the data processing unit 104. The positional information 104b detected by the position recognition unit 102b also may be transmitted to the data processing unit 104.

In such a case, the thickness dimension of the wavelength conversion unit which is the processing object can be calculated from the difference between the information 104c relating to the thickness dimension of the substrate 10 and the information relating to the thickness dimension of the components of the substrate 10 other than the wavelength conversion unit.

A processing table 103a, a tool position detection unit 103b, a tool drive unit 103c, a moving unit 103d, a cutting fluid supply unit 103e, a cutting fluid recovery unit 103f, and the like are provided in the processing unit 103. The processing unit 103 performs processing of the front surface side of the substrate 10 (the front surface side of the wavelength conversion unit) based on processing information 104d from the data processing unit 104 and based on information relating to the tip position of a tool 106 from the tool position detection unit 103b.

A holding unit 103a1 for placing and holding the holder 105a that holds the substrate 10 is provided at the processing table 103a. The holding unit 103a1 may be similar to the holding unit 102a described above.

The tool position detection unit 103b detects the information relating to the tip position of the tool 106 mounted to the tool drive unit 103c. For example, a non-contact tool length measuring apparatus and the like are examples of the tool position detection unit 103b. The relative positional relationship between the front surface position of the wavelength conversion unit and the tip position of the tool 106 can be known by the tip position of the tool 106 being detected by the tool position detection unit 103b. An automatic tool changing apparatus (ATC (Automatic Tool Changer)) 107 also may be provided to replace the tool 106 in the case where the wear of the tool 106 is confirmed by detection by the tool position detection unit 103b.

The tool drive unit 103c illustrated in FIG. 4 and FIG. 5 rotates the mounted tool 106. In such a case, the tool 106 may be mounted via a chuck 103c1 (e.g., a collet chuck, a shrink-fit chuck, etc.). A bearing structure having high rotational precision is employed to ensure the processing precision. For example, a non-contact bearing structure such as an aerostatic bearing, a hydrostatic bearing, etc., are examples of such a bearing structure.

A cooling unit 103c2 may be provided to supply air, water, and the like to the tool drive unit 103c to suppress displacement (thermal displacement) due to the heat generated when rotating the tool 106.

The tool drive unit 103c also may function as a shuttle unit to provide rapid movement of the tool 106, a FTS (Fast Tool Servo) to provide micro driving of the tool 106, and the like.

The phosphor described above is hard. Therefore, the tool 106 may have a tool tip that uses a hard material (e.g., single crystal diamond, sintered diamond, cBN (Cubic Boron Nitride), superfine cemented carbide, etc.). In such a case, if the tool 106 has a tool tip that uses a single crystal diamond, the tool tip configuration may be polished to have nanometer-order sharpness.

The moving unit 103d changes the relative positions of the tool 106 and the wavelength conversion unit. For example, the position of the tool 106 may be configured to change in at least three axis directions (the X-axis direction, the Y-axis direction, and the Z-axis direction). A not-illustrated precision guide unit (e.g., a hydrostatic guide, an aerostatic guide, a precision linear guide, etc.), a not-illustrated precision drive unit (e.g., a hydrostatic screw, an aerostatic screw, a precision ball screw, a linear motor, etc.), and the like may be provided in the moving unit 103d. In such a case, it is favorable for the position of the tool 106 to have sub-micron order changes to realize high processing precision; and it is favorable for the least input increment of the command value when changing the position of the tool 106 to be not more than 0.1 μm.

There is a risk that powder-like chips may scatter at the processing point proximity.

Therefore, the cutting fluid supply unit 103e may be provided to supply a cutting fluid to suppress the scattering of the chips at the processing point proximity; and the cutting fluid recovery unit 103f may be provided to recover the cutting fluid supplied to the processing point proximity.

A liquid feed unit 103e1 that contains and feeds the cutting fluid, a nozzle 103e2 that squirts the cutting fluid, and a flexible pipe 103e3 that connects the liquid feed unit 103e1 to the nozzle 103e2 are provided in the cutting fluid supply unit 103e.

In such a case, a not-illustrated tank that contains the cutting fluid, a not-illustrated pump that feeds the cutting fluid, a not-illustrated temperature control unit that controls the cutting fluid to have a prescribed temperature, and the like are provided in the liquid feed unit 103e1.

The cutting fluid is not particularly limited; and a cutting fluid that does not easily affect the components included in the semiconductor light emitting device 1 may be appropriately selected. For example, water, water to which various additive agents such as a surfactant, etc., are added, and the like are examples of the cutting fluid.

For example, a unit that uses vacuum suction to recover the chips together with the cutting fluid supplied to the processing point proximity is an example of the cutting fluid recovery unit 103f.

The cleanliness of the processing unit 103 can be maintained by providing the cutting fluid supply unit 103e and the cutting fluid recovery unit 103f.

Although the case is illustrated where the tool 106 is a rotating tool, this is not limited thereto. The tool 106 also may be a non-rotating tool such as an R bite, a flat bite, etc. In the case where the non-rotating tool is used, the tool drive unit 103c, the moving unit 103d, and the like may have structures to perform so-called planer cutting.

The data processing unit 104 makes the processing information 104d for performing the processing of the processing unit 103 and outputs the processing information 104d that is made toward the processing unit 103.

For example, the data processing unit 104 determines the processing information 104d relating to the thickness direction of the wavelength conversion unit based on the information 104c relating to the measured thickness dimension of the substrate and based on the information relating to the characteristic of the light emitted from the light emitting unit.

Information 104a relating to the characteristic of the light emitted from the light emitting unit 2, the positional information 104b of the substrate 10 detected by the position recognition unit 102b, and the information 104c relating to the thickness dimension of the substrate 10 measured by the measuring unit 102c may be input to the data processing unit 104.

Figure 6:
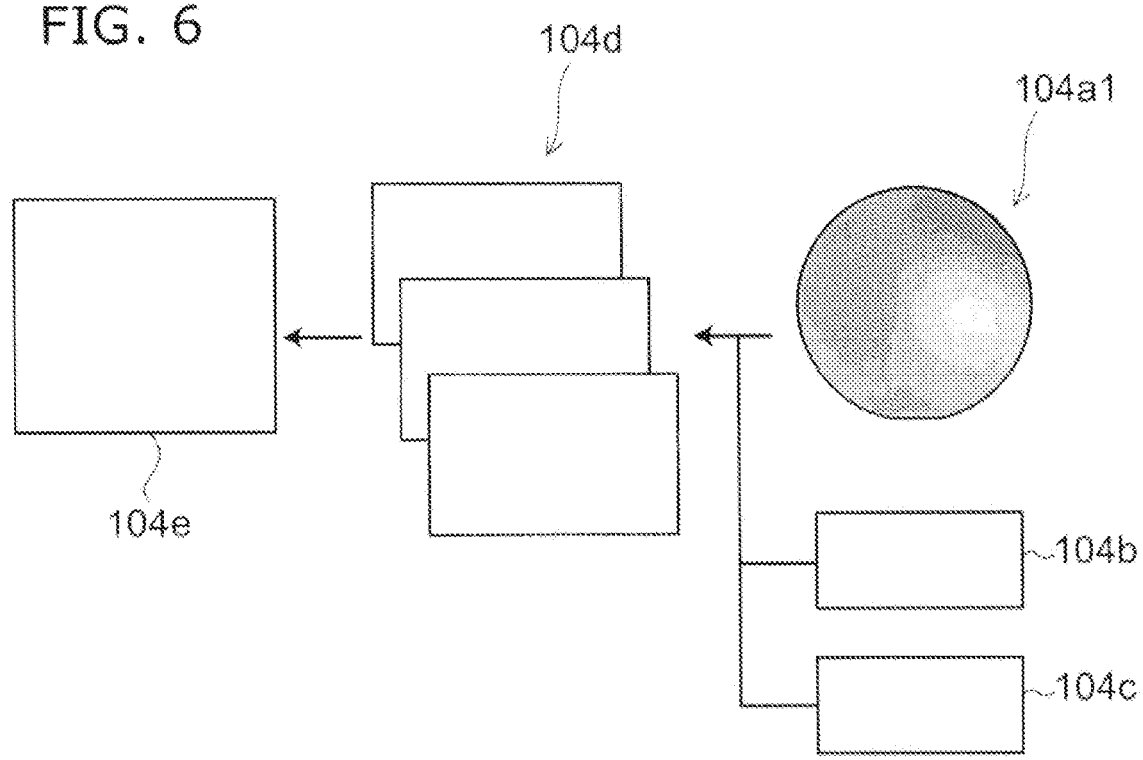
FIG. 6 is a schematic view illustrating the appearance of the processing of the data processing unit 104.

FIG. 6 is a schematic view illustrating the appearance of the processing of the data processing unit 104.

FIG. 6 is a case where the information 104a relating to the characteristic of the light emitted from the light emitting unit 2 is information 104a1 relating to the wavelength unevenness of the light emitted from the light emitting unit 2.

The information 104a1 relating to the wavelength unevenness of the light emitted from the light emitting unit 2 can be made based on the wavelength measured for each of the light emitting units 2 by a not-illustrated wavelength measuring apparatus. Then, for example, the correlation between the wavelength of the light and the chromaticity unevenness such as that illustrated in FIGS. 3A and 3B can be predetermined by experiments, and simulations, and the like; and the data processing unit 104 can determine the information relating to the chromaticity unevenness from the information 104a1 relating to the wavelength unevenness of the light and from the correlation between the wavelength of the light and the chromaticity unevenness.

Also, the data processing unit 104 can determine the distribution of the amount of the phosphor to reduce the chromaticity unevenness from the determined information relating to the chromaticity unevenness and from the correlation between the amount of the phosphor and the chromaticity that is predetermined by the experiments, the simulations, and the like; and the data processing unit 104 can determine the processing information 104d relating to the thickness direction of the wavelength conversion unit from the determined distribution of the amount of the phosphor and from the mixture proportion of the phosphor in the wavelength conversion unit to reduce the chromaticity unevenness.

The data processing unit 104 can determine the processing information 104d relating to the thickness direction of the wavelength conversion unit as follows in the case where the information 104a relating to the characteristic of the light emitted from the light emitting unit 2 is information relating to the chromaticity unevenness determined by electroluminescence (EL) spectroscopy or photoluminescence spectroscopy.

In such a case, the information relating to the chromaticity unevenness can be determined by measuring the chromaticity for each of the light emitting units 2.

Then, similarly to the case described above, the data processing unit 104 can determine the distribution of the amount of the phosphor from the information relating to the chromaticity unevenness and from the correlation between the chromaticity and the amount of the phosphor to reduce the chromaticity unevenness; and the data processing unit 104 can determine the processing information 104d relating to the thickness direction of the wavelength conversion unit from the determined distribution of the amount of the phosphor and from the mixture proportion of the phosphor in the wavelength conversion unit to reduce the chromaticity unevenness.

In such a case, the processing information 104d relating to the thickness direction of the wavelength conversion unit can be made for each of the substrates 10 by determining the information relating to the thickness dimension of the wavelength conversion unit from the distribution of the amount of the phosphor and from the mixture proportion of the phosphor in the wavelength conversion unit and by determining the processing amount from the difference between the determined information relating to the thickness dimension of the wavelength conversion unit and the thickness dimension of the wavelength conversion unit which is the processing object calculated from the information 104c relating to the thickness dimension of the substrate 10. The positional information 104b of the substrate 10 may be appropriately used when making the processing information 104d.

The processing information 104d that is made is stored in a storage unit 104e and may be output toward the processing unit 103 if necessary.

The information relating to the tool 106 (e.g., the configuration, the size, the material properties, and the like of the tool 106), the information relating to the processing conditions, and the like may be added to the processing information 104d. The processing information 104d, the added information such as the information relating to the tool 106, and the like also may be specified using a processing recipe and the like.

FIGS. 7A to 7D are schematic cross-sectional views illustrating forms of wavelength conversion units for which the processing has been performed.

Figure 7A:
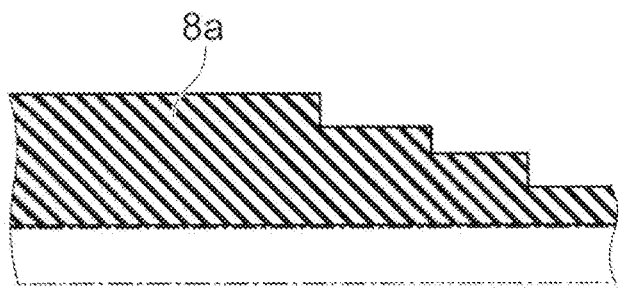
FIGS. 7A to 7D are schematic cross-sectional views illustrating forms of wavelength conversion units for which the processing has been performed.
Figure 7B:
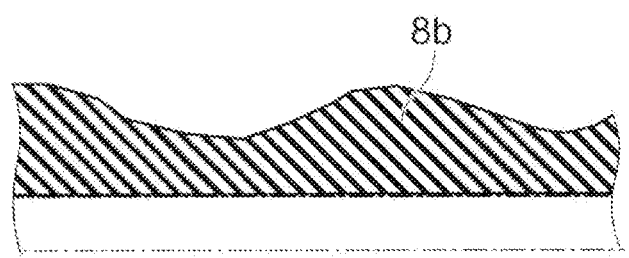
Figure 7C:
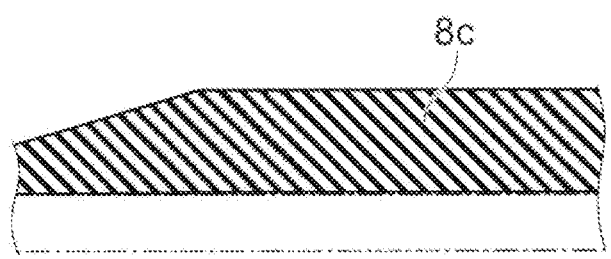
Figure 7D:
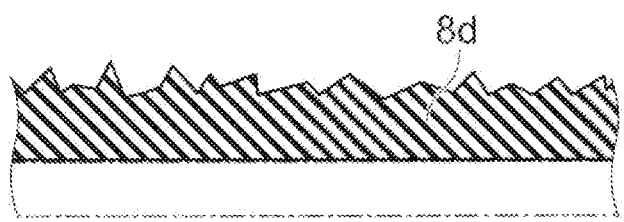

As illustrated in FIG. 7A, processing may be performed such that the front surface side of a wavelength conversion unit 8a has a stairstep configuration. As illustrated in FIG. 7B, processing may be performed such that the front surface side of a wavelength conversion unit 8b has a curved configuration. As illustrated in FIG. 7C, processing may be performed such that the front surface side of a wavelength conversion unit 8c has a tilted surface configuration. As illustrated in FIG. 7D, processing may be performed such that the front surface side of a wavelength conversion unit 8d has a hole configuration having bottoms.

The forms of the processed wavelength conversion units are not limited to those illustrated and may be modified appropriately.

Here, the front surface of the processed substrate 10a may be cleaned because chips and the like remain on the front surface of the substrate 10a.

In the case illustrated in FIG. 4, the front surface of the substrate 10a is cleaned by a cleaning unit 110 provided in the detection unit 102; and the cleaned substrate 10a is dried by a drying unit 111.

The cleaning unit 110 may include, for example, a not-illustrated tank that contains the cleaning liquid, a not-illustrated pump that feeds the cleaning liquid, a nozzle 110a that squirts the cleaning liquid, a not-illustrated flexible pipe connecting a not-illustrated pump to the nozzle 110a, and the like.

The cleaning liquid is not particularly limited; and a cleaning liquid that does not easily affect the components included in the semiconductor light emitting device 1 may be appropriately selected. For example, water, water to which various additive agents such as a surfactant, etc., are added, and the like are examples of the cleaning liquid.

For example, the drying unit 111 may dry the cleaned substrate 10a by blowing dry air and the like.

Although the case is illustrated where the cleaning unit 110 and the drying unit 111 are provided in the detection unit 102, this is not limited thereto. For example, the cleaning unit 110 and the drying unit 111 may be provided in the processing unit 103; and the drying unit 111 may be provided separately.

The cleaning unit 110 and the drying unit 111 are not limited to those illustrated and may be modified appropriately. For example, a single-wafer cleaning apparatus such as a spin cleaning apparatus, etc., may be used; and a batch cleaning apparatus that cleans by immersing multiple substrates 10a may be used.

The holder 105a that holds the substrate 10a for which the cleaning and the drying are completed is contained in the carrier 105c. Then, as described above, the carrier 105c in which the holder 105a that holds the substrate 10a is contained is transferred from the placement unit 101 to the attaching/removing unit 105.

A not-illustrated transfer unit may be provided to transfer the carrier 105c and the holder 105a that holds the substrate 10 or the substrate 10a between the placement unit 101, the detection unit 102, the processing unit 103, the attaching/removing unit 105. For example, an industrial robot and the like are examples of the not-illustrated transfer unit.

An air curtain and the like may be provided to maintain the cleanliness of the space where the placement unit 101, the detection unit 102, the processing unit 103, and the attaching/removing unit 105 are provided; and a temperature control unit and the like may be provided to maintain the temperature at a prescribed value for the space where the placement unit 101, the detection unit 102, the processing unit 103, and the attaching/removing unit 105 are provided. In such a case, at least the maintaining of the detection unit 102 and the processing unit 103 at the prescribed temperature is performed to suppress the displacement (the thermal displacement) due to the heat.

Second Embodiment

A substrate processing method that can suppress the chromaticity unevenness of the semiconductor light emitting device 1 will now be illustrated.

For example, the substrate processing method may include a process of measuring information relating to the thickness dimension of a substrate including a wavelength conversion unit that includes a phosphor, a process of determining processing information relating to the thickness direction of the wavelength conversion unit based on the measured information relating to the thickness dimension of the substrate and based on information relating to a characteristic of light emitted from the light emitting unit, and a process of processing the wavelength conversion unit based on the determined processing information.

In such a case, the information relating to the characteristic of the light emitted from the light emitting unit may be information relating to the wavelength unevenness of the light.

The process of determining the processing information described above may include determining the information relating to the chromaticity unevenness from the information relating to the wavelength unevenness of the light and from the correlation between the wavelength of the light and the chromaticity unevenness, and determining a distribution of the amount of the phosphor from the determined information relating to the chromaticity unevenness and from the correlation between the chromaticity and the amount of the phosphor to reduce the chromaticity unevenness.

Subsequently, the processing information relating to the thickness direction of the wavelength conversion unit can be determined from the determined distribution of the amount of the phosphor and from the mixture proportion of the phosphor in the wavelength conversion unit.

The information relating to the characteristic of the light emitted from the light emitting unit may be the information relating to the chromaticity unevenness.

In such a case, the process of determining the processing information described above may include determining the distribution of the amount of the phosphor from the information relating to the chromaticity unevenness and from the correlation between the chromaticity and the amount of the phosphor to reduce the chromaticity unevenness.

Subsequently, the processing information relating to the thickness direction of the wavelength conversion unit can be determined from the determined distribution of the amount of the phosphor and from the mixture proportion of the phosphor in the wavelength conversion unit.

Because the content of the method in the process of determining the processing information may be similar to the content of the processing of the data processing unit 104 described above, a detailed description is omitted.

The process of processing the wavelength conversion unit may include a process of detecting information relating to the tip position of the tool and a process of processing the wavelength conversion unit based on the processing information described above and based on the detected information relating to the tip position of the tool.

The process of processing the wavelength conversion unit may further include a process of supplying a cutting fluid that suppresses the scattering of chips at the processing point proximity.

Because the content of the method of the process of processing the wavelength conversion unit may be similar to the recited content of the processing unit 103 described above, a detailed description is omitted.

A process of causing the substrate to be held by a holder, a process of removing the processed substrate from the holder, and the like may be further included.

Also, processes having content similar to the recited content of the substrate processing system 100 described above may be further included.

Third Embodiment

A substrate processing program that can suppress the chromaticity unevenness of the semiconductor light emitting device 1 will now be illustrated.

For example, a computer capable of implementing the substrate processing program may include a processor configured to execute various information processing, a temporary storage unit such as RAM (Random Access Memory) that temporarily stores information, an input/output unit that controls sending and receiving of the information, a storage unit in which the substrate processing program is stored, and the like. Because known technology can be applied to the components included in the computer, a detailed description is omitted.

In such a case, the computer capable of implementing the substrate processing program may be included in, for example, the data processing unit 104 described above.

To execute a series of substrate processing, the substrate processing program is stored in the storage unit provided in the computer. For example, the substrate processing program may be supplied to the computer in the state of being stored in a recording medium and then read to be stored in the storage unit provided in the computer. The substrate processing program also may be stored in the storage unit provided in the computer via a LAN (Local Area Network) and the like.

Then, the substrate processing program stored in the storage unit is read into the temporary storage unit; and various operations are performed by the processor. At this time, necessary information may be input from an input unit; and the operation results and the like may be displayed by a display unit if necessary. For example, the information relating to the thickness dimension of the substrate including the wavelength conversion unit that includes the phosphor described above, the information relating to the characteristic of the light emitted from the light emitting unit, and the like are examples of the information input from the input unit.

In such a case, a substrate processing program that executes the following methods may be stored in the storage unit.

(1) A method for collecting information relating to the thickness dimension of the substrate including the wavelength conversion unit that includes the phosphor (2) A method for collecting the information relating to the characteristic of the light emitted from the light emitting unit (3) A method for calculating processing information relating to the thickness direction of the wavelength conversion unit based on the collected information relating to the thickness dimension of the substrate and based on the collected information relating to the characteristic of the light emitted from the light emitting unit (4) A method for outputting the calculated processing information Because the content of the methods may be similar to that illustrated in the substrate processing system 100 and the substrate processing method described above, a detailed description is omitted.

The substrate processing program may be executed sequentially according to the order described above. It is not always necessary to execute the substrate processing program sequentially; and the substrate processing program may be executed in parallel or selectively.

The substrate processing program may be processed by a single processor or may be processed by distributed processing by multiple processors.

The substrate processing program may further include methods including content similar to the recited content of the substrate processing system 100 and the substrate processing method described above.

According to the embodiments illustrated hereinabove, a substrate processing system, a substrate processing method, and a substrate processing program that can perform processing to suppress the chromaticity unevenness of a semiconductor light emitting device can be realized.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Moreover, above-mentioned embodiments can be combined mutually and can be carried out.

For example, the configurations, the dimensions, the material properties, the dispositions, the numbers, and the like of the components included in the substrate processing system 100 and the like are not limited to those illustrated and may be modified appropriately.

Although a multi-chip semiconductor light emitting device including multiple light emitting units is illustrated as the semiconductor light emitting device, application is possible for a semiconductor light emitting device that includes one light emitting unit. For example, there are cases where a planar distribution of the light emission characteristic of the light emitting unit 2 occurs and chromaticity unevenness occurs between the central portion and the circumferential edge portion of the light emitting unit 2. In such a case as well, the chromaticity unevenness can be suppressed by adjusting the distribution of the amount of the phosphor.

Further, this is applicable to the repair of a defective portion where the chromaticity unevenness is large, etc.

What is claimed is:

1. A substrate processing system, comprising:
 a measuring unit configured to measure information relating to a thickness dimension of a substrate, the substrate including a light emitting device having a plurality of light emitting units and a wavelength conversion unit, the wavelength conversion unit including a phosphor;
 a data processing unit configured to:
  determine processing information relating to a thickness dimension of the wavelength conversion unit based on the measured information relating to the thickness dimension of the substrate, previously obtained information relating to a characteristic of light emitted from the light emitting device, and previously obtained information relating to a relationship between the characteristic of light emitted from the light emitting device, the thickness dimension of the wavelength conversion unit, and a relationship between a length of the wavelength of the light and the chromaticity of light emitted from the wavelength conversion unit; and
 a processing unit configured to perform processing of the wavelength conversion unit to reduce the thickness dimension of the wavelength conversion unit based on the determined processing information such that a difference in chromaticity between adjacent ones of the light emitting units is not more than a predetermined threshold.

2. The system according to claim 1, wherein:
 the information relating to the characteristic of the light emitted from the light emitting unit is information relating to a wavelength unevenness of the light; and
 the data processing unit is configured to:
  determine information relating to an appropriate thickness dimension of the wavelength conversion unit from the information relating to the wavelength unevenness of the light and the previously obtained information relating to the relationship,
 wherein the appropriate thickness dimension of the wavelength conversion unit reduces the chromaticity unevenness.

3. The system according to claim 2, wherein:
 the processing information relating to the thickness dimension of the wavelength conversion unit includes a processing amount relating to the thickness dimension of the wavelength conversion unit; and
 the processing amount is determined by a difference between the appropriate thickness dimension of the wavelength conversion unit and a thickness dimension of the wavelength conversion unit calculated from the information relating to the thickness dimension of the substrate including the wavelength conversion unit measured by the measuring unit.

4. The system according to claim 1, wherein:
 the information relating to the characteristic of the light emitted from the light emitting unit is information relating to the chromaticity unevenness; and
 the data processing unit is configured to:
  determine information relating to an appropriate thickness dimension of the wavelength conversion unit from the information relating to the chromaticity unevenness of the light and the previously obtained information relating to the relationship,
 wherein the appropriate thickness dimension of the wavelength conversion unit reduces the chromaticity unevenness.

5. The system according to claim 4, wherein:
 the processing information relating to the thickness dimension of the wavelength conversion unit includes a processing amount relating to the thickness dimension of the wavelength conversion unit; and
 the processing amount is determined by a difference between the appropriate thickness dimension of the wavelength conversion unit and a thickness dimension of the wavelength conversion unit calculated from the information relating to the thickness dimension of the substrate including the wavelength conversion unit measured by the measuring unit.

6. The system according to claim 4, wherein the information relating to the chromaticity unevenness is determined using electroluminescence spectroscopy or photoluminescence spectroscopy.

7. The system according to claim 1, wherein the processing unit is configured to cut away the wavelength conversion unit.

8. The system according to claim 1, wherein:
 the processing unit includes
  a moving unit configured to change relative positions of a tool and the wavelength conversion unit, and
  a tool position detection unit configured to detect information relating to a tip position of the tool; and
 processing of the wavelength conversion unit is performed based on the processing information relating to the thickness dimension of the wavelength conversion unit and based on the information relating to the detected tip position of the tool.

9. The system according to claim 8, wherein the tool includes a tool tip formed from at least one type of material selected from the group consisting of single crystal diamond, sintered diamond, cBN (Cubic Boron Nitride), and superfine cemented carbide.

10. The system according to claim 8, wherein the processing unit further includes a tool drive unit configured to rotate the tool.

11. The system according to claim 10, wherein the tool drive unit has a bearing structure that is non-contact.

12. The system according to claim 10, wherein the processing unit further includes a cooling unit configured to cool the tool drive unit.

13. The system according to claim 8, wherein a least input increment of a command value to the moving unit when changing the relative positions of the tool and the wavelength conversion unit is not more than 0.1 µm.

14. The system according to claim 8, wherein the processing unit further includes:
 a cutting fluid supply unit configured to supply a cutting fluid to a processing point proximity; and
 a cutting fluid recovery unit configured to recover the cutting fluid supplied to the processing point proximity.

15. The system according to claim 1, further comprising an attaching/removing unit configured to cause the substrate to be held by a holder before processing of the wavelength conversion unit and configured to remove the substrate from the holder after the processing of the wavelength conversion unit.

16. The system according to claim 15, wherein:
the holder is a plate-like body; and
a holding unit is provided at one major surface of the holder, the holding unit being configured to hold the substrate including the wavelength conversion unit.

17. The system according to claim 16, wherein the holding unit is a tape that is adhesive.

18. The system according to claim 1, further comprising:
a cleaning unit configured to supply a cleaning liquid to a surface of the processed wavelength conversion unit; and
a drying unit configured to dry the surface of the wavelength conversion unit supplied with the cleaning liquid.

19. The system according to claim 1, wherein the predetermined threshold is not more than 0.015.

20. The system according to claim 1, wherein
the data processing unit is configured to determine x-coordinate values and y-coordinate values of chromaticity; and
the processing unit is configured to perform processing of the wavelength conversion unit to reduce the thickness dimension of the wavelength conversion unit based on the determined processing information such that a difference in x-coordinate values of chromaticity and a difference in y-coordinate values for adjacent ones of the light emitting units are each not more than the predetermined threshold.

21. The system according to claim 20, wherein the predetermined threshold is not more than 0.015.

22. A system comprising a computer and a non-transitory storage medium, the medium storing a substrate processing program when executed causes a computer to:
collect information relating to a thickness dimension of a substrate, the substrate including a light emitting device having a plurality of light emitting units and a wavelength conversion unit, the wavelength conversion unit including a phosphor;
collect information relating to a characteristic of light emitted from the light emitting device;
calculate processing information relating to a thickness dimension of the wavelength conversion unit based on the collected information relating to the thickness dimension of the substrate, based on the collected information relating to the characteristic of the light emitted from the light emitting unit, and based upon information relating to a relationship between the characteristic of light emitted from the light emitting unit, the thickness dimension of the wavelength conversion unit, and a relationship between a length of the wavelength of the light and the chromaticity of light emitted from the wavelength conversion unit;
send the processing information to a processing unit to cause the processing unit to reduce a thickness dimension of the wavelength conversion unit based on the determined processing information such that a difference in chromaticity between adjacent ones of the light emitting units is not more than a predetermined threshold; and
output the calculated processing information.

23. The system according to claim 22, wherein the predetermined threshold is not more than 0.015.

24. The system according to claim 23, wherein
the substrate processing program when executed causes the computer, to determine x-coordinated values and y-coordinate values of chromaticity; and
to perform processing of the wavelength conversion unit to reduce the thickness dimension of the wavelength conversion unit based on the determined processing information such that a difference in x-coordinate values of chromaticity and a difference in y-coordinate values for adjacent ones of the light emitting units are each not more than the predetermined threshold.

25. The system according to claim 24, wherein the predetermined threshold is not more than 0.015.

* * * * *